(12) United States Patent
Chou

(10) Patent No.: US 8,158,948 B2
(45) Date of Patent: Apr. 17, 2012

(54) SCINTILLATING CRYSTAL DETECTOR

(76) Inventor: Mitch M. C. Chou, Kaohsiung (TW)

( * ) Notice: Subject to any disclaimer, the term of this patent is extended or adjusted under 35 U.S.C. 154(b) by 0 days.

(21) Appl. No.: 12/942,137

(22) Filed: Nov. 9, 2010

(65) Prior Publication Data

US 2011/0204240 A1 Aug. 25, 2011

(30) Foreign Application Priority Data

Feb. 25, 2010 (TW) .............................. 99105440 A

(51) Int. Cl.
*G01T 1/20* (2006.01)
(52) U.S. Cl. .................................................... 250/361 R
(58) Field of Classification Search .............. 250/361 R, 250/362, 363.01, 363.02, 363.03, 363.04, 250/301.4 R
See application file for complete search history.

(56) References Cited

U.S. PATENT DOCUMENTS

2010/0078595 A1* 4/2010 Eriksson et al. ........ 252/301.6 F
* cited by examiner

*Primary Examiner* — Mark R Gaworecki
(74) *Attorney, Agent, or Firm* — Jackson IPG PLLC; Demian K. Jackson

(57) ABSTRACT

A detector using scintillating crystals is provided. The scintillating crystal is based on cerium doped lutetium yttrium orthosilicate (Ce:LYSO). With calcium (Ca) doped into Ce:LYSO, the electrovalence of Ce is further uniformly distributed. The scintillating crystal obtains high stability with 2 to 10 times greater electrical degree than that of a general scintillating crystal. Thus, radiative induction to cancer cells is improved and distribution of the cancer cells is easily figured out.

3 Claims, 2 Drawing Sheets

SCINTILLATING CRYSTAL DETECTOR

TECHNICAL FIELD OF THE DISCLOSURE

Figure 1:
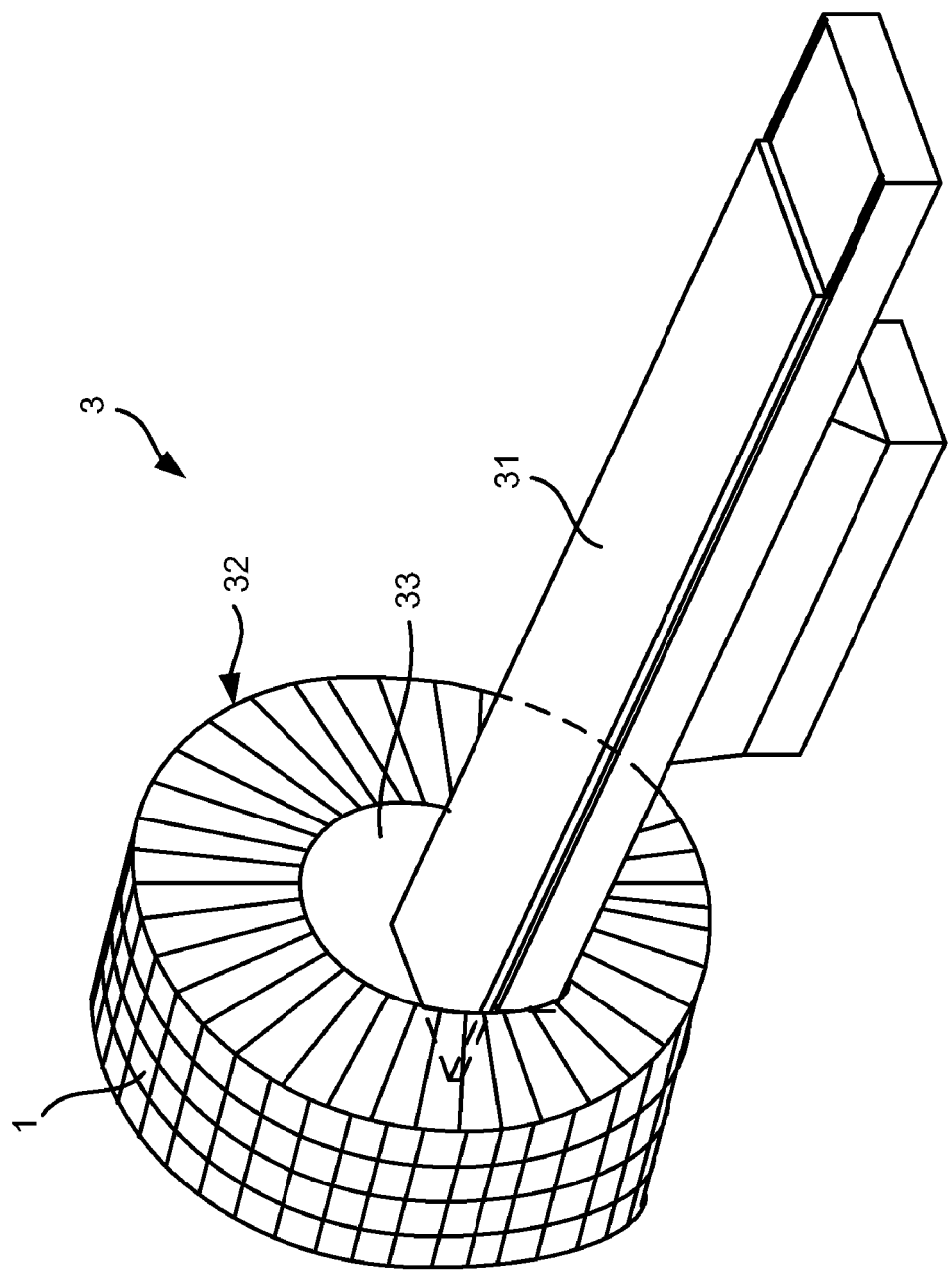

The present disclosure relates to scintillating crystal; more particularly, relates to doping calcium (Ca) atoms into cerium doped lutetium yttrium orthosilicate (Ce:LYSO) to be charge-compensated with cerium (Ce) having 4 positive electrovalence ($Ce^{+4}$) to form Ce having 3 positive electrovalence ($Ce^{+3}$) for charge balance for improved radiative induction to cancer cells owing to high energy level of Ce.

DESCRIPTION OF THE RELATED ARTS

In the modern time, tomography is widely used in clinical and biological fields. It is used to show images of dissected tissues and to observe their physiological functions. Objects of the dissected tissues are laid on a platform to be sent in a tomography machine having a circular cylinder shape for figuring out many 2-dimensional (2D) images of the objects. At last, those 2D images will be used to form 3D images.

Although tomography techniques, like computed tomography (CT) and magnetic resonance imaging (MRI), can be used to obtain a sectional image of a tissue, radiative inductions of the tomography techniques are not sensitive to cancer cells and so the cancer cells having abnormal metabolism are not detected at the first time for further preventing the cancer cells from fast divisions.

For detecting cancer cells, positron emission tomographer (PET) is usually used and the scintillating crystal used in PET is cerium doped lutetium orthosilicate (Ce:LSO). However, Ce:LSO has a high melting point, which shortens life time of crucible or melting furnace and is not easily fabricated. Besides, its cost is high. Ce:LYSO is then introduced, which has a lower melting point and a cheaper cost. Yet, lattice of Ce:LYSO is not well arranged and thus has charge defect. When it is used in PET, its charge defect will make radiation unstable and reduce photon yield owing to non-radiative energy transfer. As a result, the image obtained does not have high resolution. Hence, the prior arts do not fulfill all users' requests on actual use.

SUMMARY OF THE DISCLOSURE

The main purpose of the present disclosure is to dope Ca atoms into Ce:LYSO to be charge-compensated with $Ce^{+4}$ to form $Ce^{+3}$ for charge balance, where the present disclosure thus obtains high stability with 2 to 10 times greater electrical degree than a general scintillating crystal with a photon yield increased by reducing non-radiative energy transfer reduced yet without charges of Ce atoms changed through annealing.

The second purpose of the present disclosure is to improve radiative induction to cancer cells with improved energy level of Ce for easily figuring out distribution of the cancer cells.

To achieve the above purposes, the present disclosure is a scintillating crystal detector, comprising a scintillating crystal structure, where the scintillating crystal structure is formed by doping Ca atoms into Ce:LYSO to be charge-compensated with $Ce^{+4}$ to form $Ce^{+3}$ for uniformly distributing electrovalence of Ce in the scintillating crystal structure; and the Ca atoms are obtained from calcium oxide having a density between 0.00001 and 0.05. Accordingly, a novel scintillating crystal detector is obtained.

BRIEF DESCRIPTIONS OF THE DRAWINGS

Figure 2:
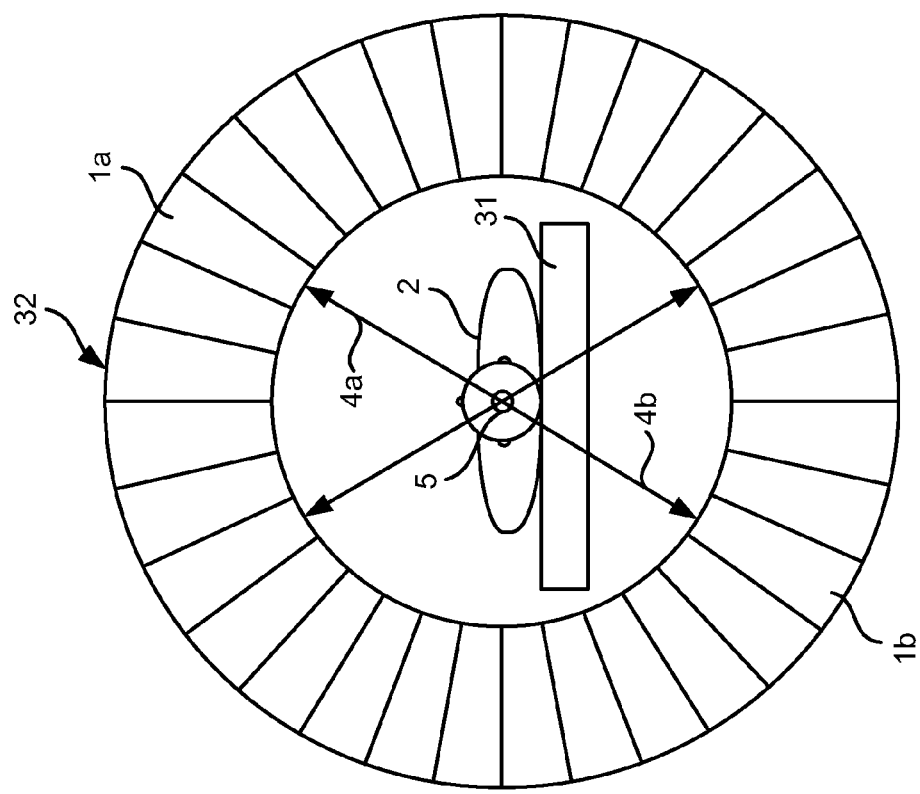

The present disclosure will be better understood from the following detailed description of the preferred embodiment according to the present disclosure, taken in conjunction with the accompanying drawings, in which:

FIG. 1 is the structural view showing the preferred embodiment according to the present disclosure; and FIG. 2 is the view showing the state of use.

DESCRIPTION OF THE PREFERRED EMBODIMENT

The following description of the preferred embodiment is provided to understand the features and the structures of the present disclosure.

Please refer to FIG. 1 and FIG. 2, which are a structural view showing a preferred embodiment according to the present disclosure; and a view showing a state of use. As shown in the figures, the present disclosure is a scintillating crystal detector 1, comprising a scintillating crystal structure. The scintillating crystal structure is formed by doping calcium (Ca) atoms into cerium doped lutetium yttrium orthosilicate (Ce:LYSO) for developing cancer cells by the scintillating crystal detector 1. Therein, the Ca atoms are obtained from calcium oxide having a density between 0.00001 and 0.05; and, the scintillating crystal structure can be formed by doping magnesium (Mg) atoms into cerium doped lutetium yttrium orthosilicate (Ce:LYSO). When a to-be-detected object 2 having cancer cells is detected by the scintillating crystal detector 1, the cancer cells in the to-be-detected object 2 are detected by the strong radiative induction of the scintillating crystal structure; and, distribution of the cancer cells in the to-be-detected object 2 is thus sensitively figured out in a high-resolution image.

On using the present disclosure, the scintillating crystal detector 1 is set in a positron emission tomo-grapher (PET) 3. The PET 3 comprises a platform 31 for holding the to-be-detected object 2; a circular cylindrical shadow mask 32; and a plurality of the scintillating crystal detectors 1 freely distributed in the shadow mask 32. On using the PET 3 having the scintillating crystal detectors 1, the to-be-detected object 2 is laid on the platform 31 and the platform 31 is slowly move through a scan channel 33 formed by the shadow mask 32. Then, the tens or even hundreds of scintillating crystal detectors 1 surrounding the shadow mask start to detect the to-be-detected object 2 simultaneously. If two scintillating crystal detectors 1a, 1b at two corresponding positions simultaneously detect two photons 4a, 4b generated from an annihilation radiation from positron emitter in the to-be-detected object 2, a direct line passing through a photogenic cell 5 is defined. With multiple intersected lines, each cell has its position and metabolic rate thus defined.

Hence, by doping with Ca atoms according to the present disclosure, charge compensation occurs. Therein, Ca atoms are charge-compensated with $Ce^{+4}$ to form $Ce^{+3}$ in Ce:LYSO to distribute electrovalence of Ce in the scintillating crystal structure uniformly. Charge balance in the Ce:LYSO is thus further compensated to obtain 2 to 10 times greater electrical degree than general scintillating crystal as well as higher stability. As a result, according to the present disclosure, a photon yield is increased by reducing non-radiative energy transfer; radiative induction to cancer cells is improved with higher energy level of Ce; and, the scintillating crystal detectors 1 figure out distribution of cancer cells without charges of the Ce atoms changed through annealing.

To sum up, the present disclosure is a scintillating crystal detector, where Ca atoms are doped for charge compensation with $Ce^{+4}$ to form $Ce^{+3}$ and electrovalence of Ce is uniformly distributed in scintillating crystal with greater electrical degree generated; photon yield is increased by non-radiative energy transfer; radiative induction to cancer cells is improved; and distribution of cancer cells is figured out easily.

The preferred embodiment herein disclosed is not intended to unnecessarily limit the scope of the disclosure. Therefore, simple modifications or variations belonging to the equivalent of the scope of the claims and the instructions disclosed herein for a patent are all within the scope of the present disclosure.

What is claimed is:

1. A scintillating crystal detector, comprising:
a scintillating crystal structure, said scintillating crystal structure being obtained by doping calcium (Ca) atoms into cerium doped lutetium yttrium orthosilicate (Ce:LYSO),
wherein said Ca atoms are obtained from calcium oxide having a density between 0.00001 and 0.05.

2. The detector according to claim 1,
wherein said Ca atoms have charge compensation with cerium atoms (Ce) having 4 positive electrovalence ($Ce^+_4$) in Ce:LYSO to obtain Ce atoms having 3 positive electrovalence ($Ce^{+3}$) and thus electrovalence of Ce is uniformly distributed in said scintillating crystal structure.

3. The detector according to claim 1,
wherein a plurality of said scintillating crystal detectors is put in a positron emission tomographer (PET).

* * * * *